(12) United States Patent
Moitzi

(10) Patent No.: US 10,352,841 B2
(45) Date of Patent: Jul. 16, 2019

(54) DETERMINATION OF A REFRACTIVE INDEX OF A SAMPLE AND OF A PARTICLE SIZE OF PARTICLES IN SAID SAMPLES BY MEANS OF A DYNAMIC LIGHT SCATTERING APPARATUS

(71) Applicant: Anton Paar GmbH, Graz (AT)

(72) Inventor: Christian Moitzi, Raaba (AT)

(73) Assignee: Anton Paar GmbH, Graz (AT)

( * ) Notice: Subject to any disclaimer, the term of this patent is extended or adjusted under 35 U.S.C. 154(b) by 47 days.

(21) Appl. No.: 15/528,437

(22) PCT Filed: Nov. 20, 2015

(86) PCT No.: PCT/EP2015/077196
§ 371 (c)(1),
(2) Date: May 19, 2017

(87) PCT Pub. No.: WO2016/079286
PCT Pub. Date: May 26, 2016

(65) Prior Publication Data
US 2018/0313737 A1    Nov. 1, 2018

(30) Foreign Application Priority Data

Nov. 21, 2014 (EP) .................................... 14194341

(51) Int. Cl.
*G01N 15/02* (2006.01)
*G01N 21/51* (2006.01)
(Continued)

(52) U.S. Cl.
CPC ......... *G01N 15/0211* (2013.01); *G01N 21/51* (2013.01); *G01N 2015/0046* (2013.01);
(Continued)

(58) Field of Classification Search
CPC ....... G01N 15/0211; G01N 2015/0222; G01N 2015/0046; G01N 2015/0053; G01N 21/51; G01N 2021/4153; G01N 2021/4726
See application file for complete search history.

(56) References Cited

U.S. PATENT DOCUMENTS

| 4,983,040 A | 1/1991 | Chu et al. |
| 5,126,581 A | 6/1992 | Furuya et al. |

(Continued)

FOREIGN PATENT DOCUMENTS

| DE | 102008007743 B3 | 5/2009 |
| EP | 0334536 A2 | 9/1989 |
| EP | 0 344 536 A1 | 12/1989 |

OTHER PUBLICATIONS

Benjamin Chu et al., "Prism laser light-scattering spectrometer," Review of Scientific Instruments, vol. 59, No. 5, May 1988, pp. 716-724, XP055185619, American Institute of Physics.
(Continued)

*Primary Examiner* — Sang H Nguyen
(74) *Attorney, Agent, or Firm* — Robert A. Blaha; Smith Tempel Blaha LLC

(57) ABSTRACT

A dynamic light scattering apparatus includes a source configured for irradiating a sample with primary electromagnetic radiation, a detector configured for detecting secondary electromagnetic radiation generated by scattering the primary electromagnetic radiation at the sample, a refraction index determination unit including a movable optical element and configured to determine information indicative of a refraction index of the sample based on measurements of the secondary electromagnetic radiation for a plurality of different positions of the movable optical element, and a particle size determining unit configured to determine information indicative of particle size of particles in the sample
(Continued)

by analyzing the detected secondary electromagnetic radiation and taking into account the refraction index determined by the refraction index determining unit.

10 Claims, 12 Drawing Sheets

(51) Int. Cl.
  *G01N 21/41* (2006.01)
  *G01N 21/47* (2006.01)
  *G01N 15/00* (2006.01)

(52) U.S. Cl.
  CPC ............ *G01N 2015/0053* (2013.01); *G01N 2015/0222* (2013.01); *G01N 2021/4153* (2013.01); *G01N 2021/4726* (2013.01)

(56) References Cited

U.S. PATENT DOCUMENTS

| | | | |
|---|---|---|---|
| 5,257,087 A * | 10/1993 | Furuya | G01N 15/0205 356/335 |
| 5,506,673 A * | 4/1996 | Kosaka | G01N 15/12 356/336 |
| 5,696,580 A | 12/1997 | Kubo et al. | |
| 5,859,705 A * | 1/1999 | Benedetto | G01N 15/0205 356/336 |
| 5,907,399 A * | 5/1999 | Shirasawa | G01N 15/0205 356/336 |
| 7,105,849 B2 | 9/2006 | Prelewitz | |
| 7,430,046 B2 * | 9/2008 | Jiang | G01N 15/0205 356/336 |
| 7,999,936 B1 | 8/2011 | Li et al. | |
| 8,705,036 B2 * | 4/2014 | Peters | G01N 21/51 356/337 |
| 9,243,892 B2 * | 1/2016 | Tochino | G01N 15/0211 |
| 9,297,736 B2 * | 3/2016 | Sugasawa | G01N 15/0211 |
| 9,857,283 B1 * | 1/2018 | Tatarkiewicz | G01N 15/0227 |
| 2013/0176556 A1 * | 7/2013 | Larkin | G01N 21/01 356/73 |

OTHER PUBLICATIONS

The State Intellectual Property Office of Peoples Republic of China, Office Action in Application No. 201580074042.2, dated Mar. 12, 2019, 7 pp., English translation thereof 3 pp.

* cited by examiner

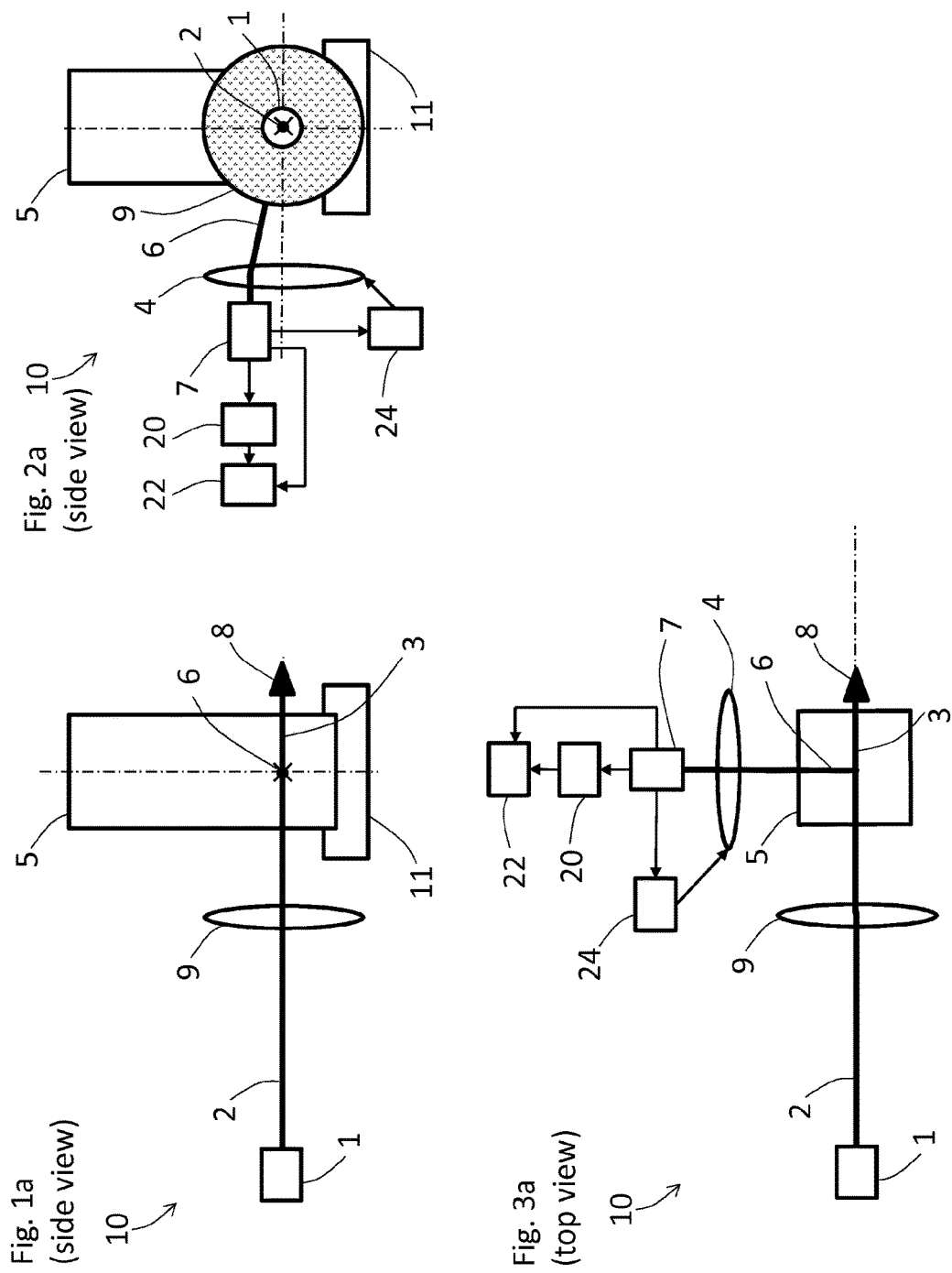

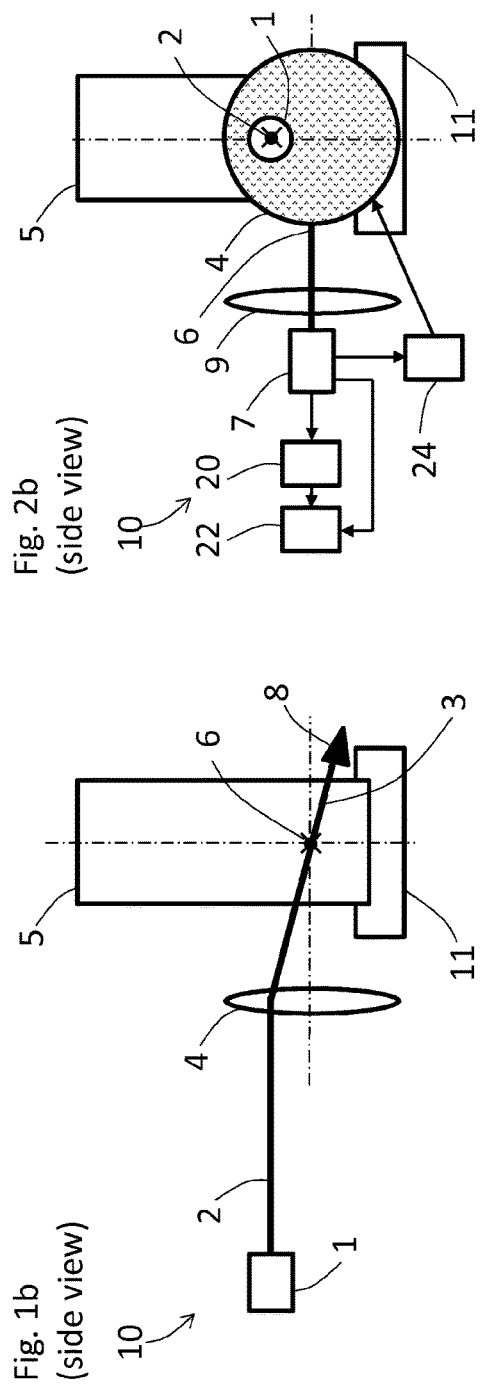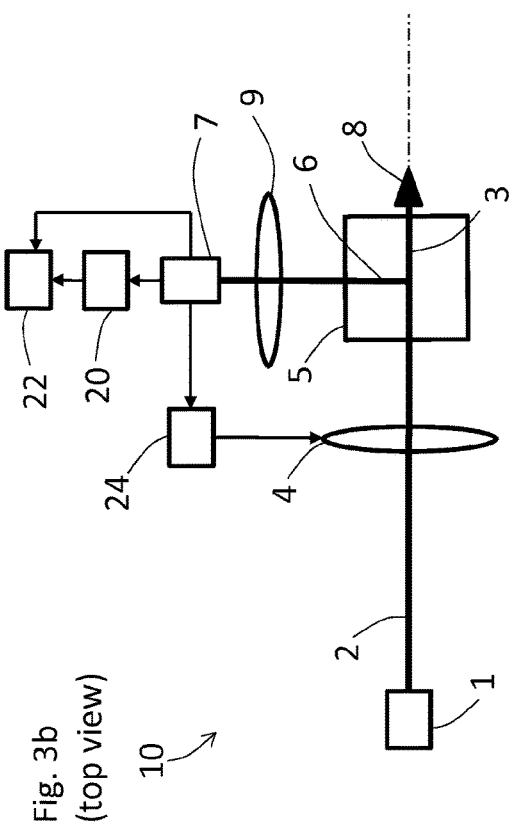

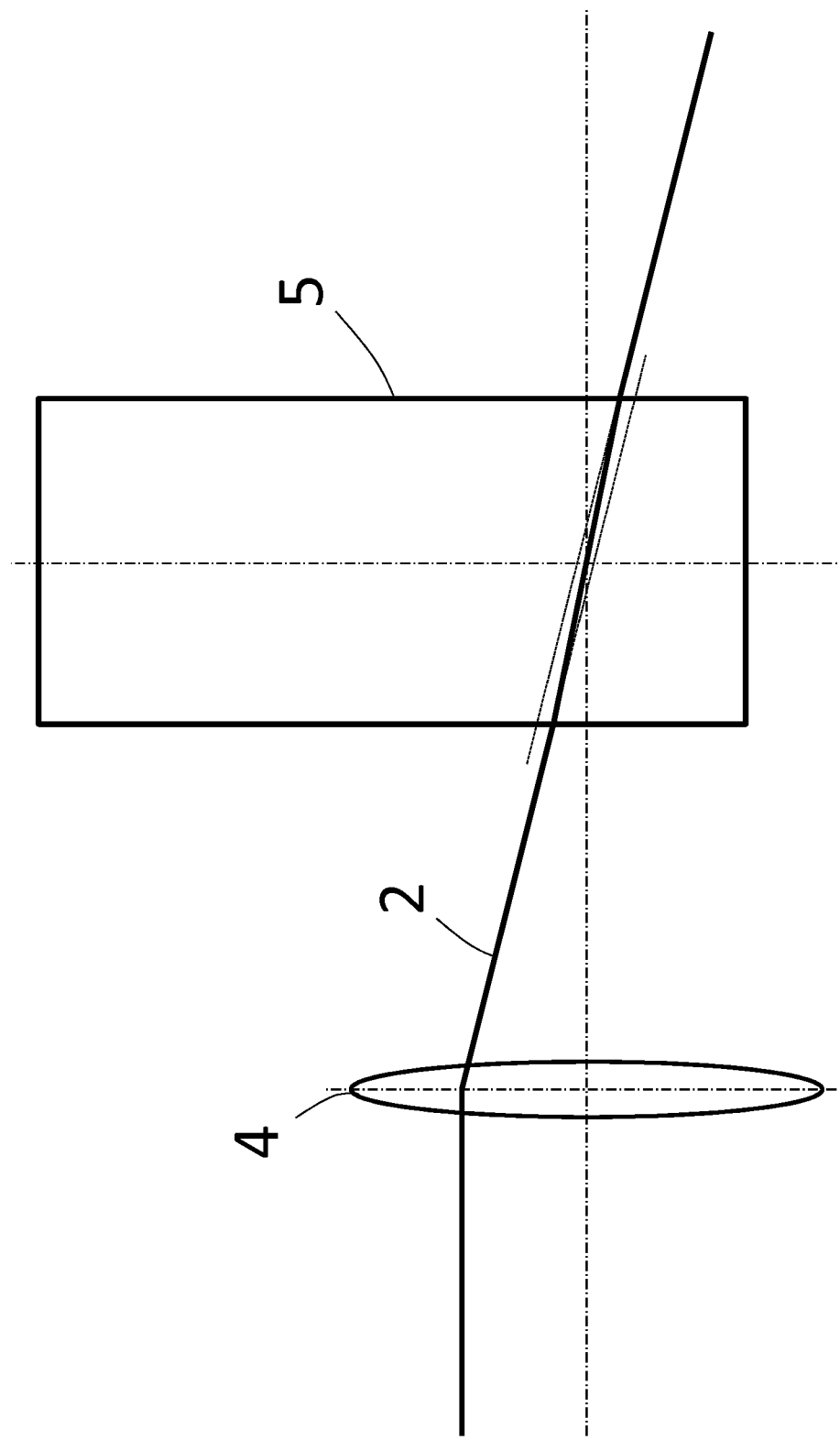

DETERMINATION OF A REFRACTIVE INDEX OF A SAMPLE AND OF A PARTICLE SIZE OF PARTICLES IN SAID SAMPLES BY MEANS OF A DYNAMIC LIGHT SCATTERING APPARATUS

CROSS-REFERENCE TO RELATED APPLICATIONS

This application is a national phase application of international patent application PCT/EP2015/077196, which claims the benefit of the filing date of European Patent Application No. 14194341.5, filed on Nov. 21, 2014, the disclosure of which is hereby incorporated herein by reference in its entirety.

TECHNICAL FIELD

Embodiments of the invention relate to scattering apparatuses.

Furthermore, embodiments of the invention relate to methods of determining information indicative of particle size of particles in a sample by scattering.

TECHNOLOGICAL BACKGROUND

Reference is made to U.S. Pat. Nos. 5,126,581, 5,696,580, 7,999,936, 7,105,849, and DE 10 2008 007 743.

For analyzing a fluidic sample, the fluidic sample may be filled into a sample container. An electromagnetic radiation beam may then be brought in interaction with the fluidic sample, wherein the scattered electromagnetic radiation beam may then carry information indicative of physical and/or chemical properties of the fluidic sample. Such an arrangement may be used for determining the particle size by dynamic light scattering (DLS).

By DLS, particle sizes in dispersions may be determined. An advantage of the DLS method is that only a very limited knowledge with regard to the properties of the sample is sufficient. However, the value of the refraction index of the sample (in particular of the solvent thereof) and the viscosity thereof are required as input parameters. Hence, a user has to input manually in a DLS apparatus which refraction index a sample under investigation (in particular a solvent thereof) is used. For example, a user may use a database with values of the refraction index for frequently used solvents as a function of the measurement temperature. The user must select a solvent or must manually input a corresponding numerical value for the refraction index. The same applies to viscosity. However, it is possible to determine viscosity by DLS when all other parameters (i.e. also particle size) are known. The so-called Zetasizer from Malvern Instruments Ltd, which is commercially available, has an integrated method for determining viscosity which is also denoted as microrheology.

In view of the foregoing, the value of the refraction index or the used solvent must be known for DLS. When the solvent is however not known, not available in a database, or is strongly temperature-dependent, it is necessary for a user to first measure the refraction index with a separate device, for instance with the so-called refractometer Abbemat of Anton Paar GmbH.

A further shortcoming of conventional DLS apparatuses is that, for example as a consequence of a long-term drift of the DLS apparatus, the latter may drift out of a desired operation condition under which a measured intensity of a detection signal has a pronounced value. This may result in a deterioration of the measurement accuracy or requires a user in a cumbersome way to readjust the value manually.

Concluding, there is still room for improving accuracy of conventional DLS apparatuses. Moreover, there is still room for improving user-convenience when operating DLS apparatuses.

SUMMARY

There may be a need to enable scattering experiments to be performed in a user-friendly way and/or with high accuracy regardless of which sample is used.

In order to meet the need defined above, apparatuses and methods according to the independent claims are provided.

According to an exemplary embodiment of the invention, a scattering apparatus (in particular a dynamic light scattering (DLS) apparatus) is provided which comprises an electromagnetic radiation source configured for irradiating a sample with primary electromagnetic radiation, an electromagnetic radiation detector configured for detecting secondary electromagnetic radiation generated by scattering the primary electromagnetic radiation at the sample, a refraction index determination unit configured for determining information indicative of a refraction index of the sample, and a particle size determining unit configured for determining information indicative of particle size of particles in the sample by analyzing the detected secondary electromagnetic radiation.

According to another exemplary embodiment of the invention, a method of determining information indicative of particle size of particles in a sample by scattering (in particular dynamic light scattering) is provided, wherein the method comprises irradiating a sample with primary electromagnetic radiation, detecting secondary electromagnetic radiation generated by scattering the primary electromagnetic radiation at the sample, determining information indicative of a refraction index of the sample (in particular using the same equipment as for determining information indicative of particle size of particles in the sample), and determining information indicative of particle size of particles in the sample by analyzing the detected secondary electromagnetic radiation.

According to another exemplary embodiment of the invention, a scattering apparatus (in particular a dynamic light scattering apparatus) is provided which comprises an electromagnetic radiation source configured for irradiating a sample with primary electromagnetic radiation, an electromagnetic radiation detector configured for detecting secondary electromagnetic radiation generated by scattering the primary electromagnetic radiation at the sample, a movable (in particular movable by a drive unit such as a motor or a piezo element of the scattering apparatus) optical element in an optical path including at least one of the primary electromagnetic radiation and the secondary electromagnetic radiation, an adjustment unit configured for moving (or controlling motion of) the optical element so as to at least partially compensate for a deviation between a maximum detection intensity (i.e. an intensity value which can be obtained in an optimum configuration of the scattering apparatus) and an actual detection intensity (i.e. an intensity value which can be obtained by a present configuration of the scattering apparatus), and a particle size determining unit configured for determining information indicative of particle size of particles in the sample by analyzing the detected secondary electromagnetic radiation. For instance, the adjustment can be done so that the actual detection intensity approaches or even reaches the maximum detection intensity as a result of the adjustment.

According to another exemplary embodiment of the invention, a method of determining information indicative of particle size of particles in a sample by scattering (in particular dynamic light scattering) is provided, wherein the method comprises irradiating a sample with primary electromagnetic radiation, detecting secondary electromagnetic radiation generated by scattering the primary electromagnetic radiation at the sample, moving an optical element, which is movable in an optical path including at least one of the primary electromagnetic radiation and the secondary electromagnetic radiation, so as to at least partially compensate for a deviation between a maximum detection intensity and an actual detection intensity, and determining information indicative of particle size of particles in the sample by analyzing the detected secondary electromagnetic radiation.

According to one aspect of an exemplary embodiment of the invention, a refraction index determination is carried out by a scattering-based particle size information determining apparatus itself, i.e. by integrating the refraction index measurement into such an apparatus. Thus, the value of the refraction index of the sample (more precisely a solvent in which particles to be analyzed are dispersed) is measured with the same apparatus which also determines particle size distribution or other kind of information related to particle size. Therefore, it becomes dispensable for a user to look in a database or measure separately the value of the refraction index of the sample in terms of a particle size determination experiment. This not only simplifies use of the apparatus for a user, but also improves the accuracy and reduces the risk of failure by actually measuring the refraction index on exactly the same sample and under exactly the same conditions as used for the particle size distribution analysis. Neither a transfer of the sample under analysis from a separate refraction index determination apparatus to the particle size determination apparatus is necessary, nor can any temperature effect (for instance a temperature dependence of the refraction index) deteriorate the particle size measurement accuracy.

According to another aspect of an exemplary embodiment of the invention, measurement artifacts during particle size determination may be sufficiently suppressed by an active adjustment mechanism of the apparatus. In a scenario in which for example a long-term drift of the apparatus or a sudden change of the refraction index (for instance induced by a temperature change) drives the apparatus into an operation mode in which a measurable detection signal intensity is reduced compared to an optimum configuration as a consequence of a change of the external or internal measurement conditions, the optical element may be moved by the adjustment towards another position within the measurement path so as to at least partially compensate for the reduction of the detection intensity. In other words, the system may be driven back into an operation mode with a higher detection intensity, even back into a maximum intensity measurement state.

In the context of the present application, the term "sample" may particularly denote a fluidic sample (such as a liquid and/or gaseous sample), in particular having solid particles or liquid droplets included therein. Hence, the sample under analysis may be a dispersion.

In the context of the present application, the term "refraction index" may particularly denote a temperature-dependent parameter indicative of the extent according to which an electromagnetic radiation beam changes its propagation direction when propagating from a surrounding medium (such as air) into a sample container containing the sample.

In the context of the present application, the term "electromagnetic radiation" may particularly denote photons in a suitable wavelength range. One appropriate wavelength range is the range of optical light, i.e. light of a wavelength between 400 nm and 800 nm. However, it is also possible in other embodiments to carry out the measurement with infrared radiation (i.e. having longer wavelengths than the visible range), in the ultraviolet range (i.e. in a range of wavelength being shorter than in the visible range), or in other suitable wavelength ranges.

In the following, further exemplary embodiments of the apparatuses and the methods will be explained.

In an embodiment, the refraction index determination unit is configured for determining the refraction index related information based on an analysis of the detected secondary electromagnetic radiation. According to such a highly preferred embodiment, the electromagnetic radiation beam propagating between electromagnetic radiation source and electromagnetic radiation detector via the sample with the refraction index of interest is not only used for determining particle size information, but is simultaneously used for determining the value of the refraction index of the sample (more precisely a solvent thereof). Therefore, the measurement of the refraction index can be obtained substantially without any additional hardware requirement. In contrast to this, the anyway used measurement components for measuring the particle size distribution may be synergetically used also for the determination of the refraction index. This not only keeps the apparatus compact and lightweight, but also ensures determination of the particle size and determination of the refraction index under exactly the same conditions, thereby also increasing the accuracy and the reliability.

In an embodiment, the refraction index determination unit comprises a movable (in particular movable by a drive unit such as a stepper motor) optical element in an optical path including at least one of the primary electromagnetic radiation and the secondary electromagnetic radiation (thus interacting with the electromagnetic radiation) and is configured for determining information indicative of the refraction index of the sample by analyzing an intensity variation of the detected secondary electromagnetic radiation at different positions of the movable optical element in the optical path. According to the described preferred embodiment of the invention, the optical element is moved to different positions with regard to the optical path, and the impact of this motion on the detection intensity is measured. In other words, a detection signal of the electromagnetic radiation detector is detected for different positions of the optical element with regard to the beam path. Thus, a characteristic intensity curve during motion of the optical element along a predetermined motion trajectory of the movable element can be measured. Experiments have shown that parameters (such as a position of the optical element at which a maximum intensity is obtained) of this characteristic curve accurately depends on the value of the refraction index of the sample. An analysis of the characteristic curve therefore allows to derive the value of the refraction index of the sample.

In an embodiment, the refraction index determination unit is configured for determining the information indicative of the refraction index of the sample based on a comparison of one or more features of an intensity curve (in particular a maximum intensity value, a slope of a rising edge, a slope of a falling edge, etc.) showing a correlation between optical element position and detection intensity obtained for the sample under analysis (see FIG. 8) with predetermined data of one or more reference materials (which data may comprise information regarding one or more features of a reference intensity curve for the respective reference material, in particular a maximum intensity value, a slope of a rising edge, a slope of a falling edge, etc. of a curve showing a correlation between optical element position and detection intensity obtained for the respective reference material substituting the sample, see FIG. 9). According to the described preferred embodiment, it has turned out that the determination of the refraction index is particularly precise when the position of the movable optical element relative to the beam path is determined at which the detected intensity has a maximum value. When calibration data are available for two or more reference solvents (as reference materials) with pre-known values of the refraction index, and when corresponding maximum intensity positions of the optical element are also known for these reference substances, a comparison of a maximum intensity value position of a sample presently under analysis with the maximum intensity values of the reference substances allows for a precise determination of the refraction index of the sample under analysis. Advantageously, this determination can be carried out with the same hardware components which are anyway used for the particle size distribution measurement. Also the measurement conditions for measuring the particle size information and for determining the refraction index value may be the same, so that the results are directly comparable, without an additional measurement inaccuracy introduced by an input refraction index.

In an embodiment, the optical element is selected from a group consisting of a lens, a mirror, a plate, and a wedge. It is preferred that the optical element is a double convex lens which can be moved so that a central lens axis is thereby displaced with regard to the optical path. However, as an alternative to such an optically transparent lens, another optically transparent optical element may be used such as a plano-convex lens, a double convex lens, an achromatic lens, a concave-convex lens, a plate with parallel surfaces, or a prism-like wedge. It is also possible that, in contrast to a transmissive optical element through which the electromagnetic radiation passes, an optical element having reflective properties may be used, such as a planar or curved mirror. The only necessity is that the optical element manipulates the electromagnetic radiation beam in dependence of the optical element's relative position with regard to the beam path. Hence, it is possible to use the optical element's motion to scan the spatial intensity pattern so that the maximum intensity achievable with a present sample can be obtained. It is also possible to adjust the apparatus to obtain an increased or even maximum detection intensity for compensating drift and/or ageing effects.

In an embodiment, the optical element is located between the sample and the electromagnetic radiation detector, in the beam path. Thus, the optical element may be located downstream of a sample container containing the sample under analysis but upstream of the electromagnetic radiation detector. In another embodiment, the optical element is located between the electromagnetic radiation source and the sample, in the beam path. Thus, the movable optical element may be located downstream of the electromagnetic radiation source but upstream of a sample container containing the sample.

In an embodiment, the optical element is mounted so as to be movable by at least one of the group consisting of displacing the optical element parallel to the optical path, displacing the optical element perpendicular to the optical path, and tilting the optical element relative to the optical path. Regardless as to whether the optical element is longitudinally displaced or rotated for sampling the achievable detection accuracy (to compensate for drifts and/or for determining the refraction index value) such a motion may be performed under the control of a drive unit such as an electric motor. Thus, the refraction index determination and the drift compensation can be carried out in a self-sufficient way without the requirement of a user contribution. During this motion, the signal intensity may be measured by the same electromagnetic radiation detector which is also used for determining particle size distribution.

In an embodiment, the apparatus comprises an adjustment unit configured for moving the optical element so as to at least partially compensate for a deviation between a maximum obtainable detection intensity and an actually obtained detection intensity. Therefore, in addition to the refraction index determination, the apparatus can be also used for increasing the achievable detection intensity for drift compensation, signal enhancement or other purposes.

In an embodiment, the particle size determining unit is configured for determining the information indicative of particle size under consideration of the determined information indicative of the refraction index. Therefore, the determined refraction index value information can be directly used for an algorithm of determining particle size distribution by DLS. Thus, the refraction index may be taken into account without requiring a user to manually input any inaccurate value. Furthermore, changes of the refraction index (for instance as a consequence of a temperature change) may be considered substantially in real time.

In an embodiment, the electromagnetic radiation detector is located (for detecting secondary electromagnetic radiation for determining the information indicative of the refraction index and indicative of the particle size distribution) to detect the secondary electromagnetic radiation along a secondary propagation direction which is oriented to detect beams with beam components oriented perpendicular to the primary electromagnetic radiation. More particularly, the electromagnetic radiation detector can be located to detect the secondary electromagnetic radiation along a secondary propagation direction perpendicular to a primary propagation direction along which the primary electromagnetic radiation propagates directly upstream of the sample. In other words, an orientation of the electromagnetic radiation detector may be selected so that the detected beam is perpendicular to the incident beam. With this geometry, a precise determination of the refraction index is possible, in particular by DLS.

In an embodiment, the optical element is moved so that the actual detection intensity is the maximum detection intensity. Thus, the apparatus may be driven into a condition in which the detection signal has the largest possible value, thereby allowing for a precise measurement of the particle size distribution using a precisely determined refraction index value.

The aspects defined above and further aspects of the invention are apparent from the examples of embodiment to be described hereinafter and are explained with reference to these examples of embodiment.

The invention will be described in more detail hereinafter with reference to examples of embodiment but to which the invention is not limited.

BRIEF DESCRIPTION DRAWINGS

FIG. 1a, FIG. 2a and FIG. 3a illustrate a dynamic light scattering apparatus according to an exemplary embodiment of the invention in two different side views and the top view.

FIG. 1b, FIG. 2b and FIG. 3b illustrate a dynamic light scattering apparatus according to another exemplary embodiment of the invention in two different side views and the top view.

FIG. 4 is a schematic illustration of a measurement laser when propagating through a collective lens and a measurement cell.

DETAILED DESCRIPTION OF EXEMPLARY EMBODIMENTS

Figure 5:
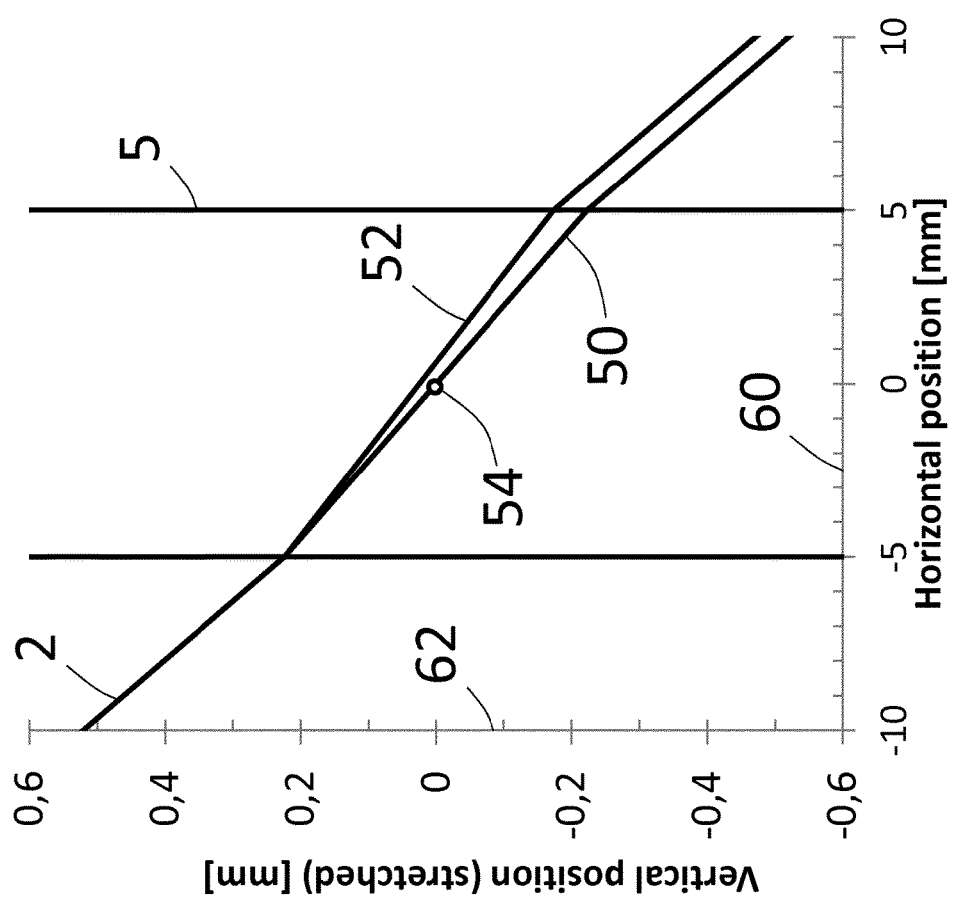
FIG. 5 is a side view of a measurement cell.

The illustrations in the drawings are schematical. In different drawings, similar or identical elements are provided with the same reference signs.

FIG. 1a, FIG. 2a and FIG. 3a illustrate a dynamic light scattering (DLS) apparatus 10 according to an exemplary embodiment of the invention from three different views.

The dynamic light scattering apparatus 10 comprises an electromagnetic radiation source 1, which is here embodied as a coherent light source such as a laser, configured for irradiating a sample 5 in a sample container (such as a cuvette) with primary electromagnetic radiation 2 in the form of a monochromatic visible light beam. The sample 5 is configured as a dispersion of liquid with particles being subject to Brownian motion. The sample 5 may hence be a dispersion of particles to be detected (in particular solid particles or liquid droplets) dispersed in a liquid solution (such as water or toluene). Between the electromagnetic radiation source 1 and an inlet window of the sample container containing the sample 5, a fixed optical element 9, here embodied as a lens, is located in the beam path. The sample container is supported by a support structure 11, which can be used for temperature control of the sample. When the primary electromagnetic radiation 2 interacts with the sample 5, the primary electromagnetic radiation 2 is scattered and is therefore modified into secondary electromagnetic radiation 6 which propagates—through an outlet window of the sample container—towards an electromagnetic radiation detector 7. Between the outlet window of the sample container containing the sample 5 and the electromagnetic radiation detector 7, a movable optical element 4, here embodied as a lens, is located in the beam path. Depending on its position relative to the beam path, the secondary electromagnetic radiation 6 is refracted by the moveable optical element 4 to a certain degree. The electromagnetic radiation detector 7, for example embodied as a light-sensitive photodetector such as a photodiode, is configured for detecting the secondary electromagnetic radiation 6.

As can be taken from FIG. 1a to FIG. 3a, the electromagnetic radiation detector 7 is located and oriented so as to selectively measure in a direction perpendicular to the incident direction of the primary electromagnetic radiation 2. As can be taken from FIG. 1a, FIG. 2a and FIG. 3a, a plane within which the primary electromagnetic radiation 2 propagates (the paper plane according to FIG. 1a) is perpendicular to a direction along which the electromagnetic radiation detector 7 detects the secondary electromagnetic radiation 6 in terms of DLS. FIG. 1a shows the dynamic light scattering apparatus 10 in a side view in which the beam of the primary electromagnetic radiation 2 lies within the paper plane, whereas the beam of the secondary electromagnetic radiation 6 is oriented perpendicular to the paper plane of FIG. 1a. According to FIG. 3a, both the primary electromagnetic radiation 2 as well as the secondary electromagnetic radiation 6 are beams which lie in the paper plane of FIG. 3a. According to FIG. 2a, the primary electromagnetic radiation 2 is oriented perpendicular to the paper plane of FIG. 2a, whereas the secondary electromagnetic radiation beam 6 is oriented in the paper plane of FIG. 2a.

The electromagnetic radiation detector 7 is a point-type detector capable of measuring the intensity of the respectively scattered light in form of the second electromagnetic radiation 6. A portion 3 of the primary electromagnetic radiation 2 which is not scattered propagates towards a beam stop 8.

A particle size determining unit 22 illustrated in FIG. 2a and FIG. 3a can for instance comprise a processor (for instance a microprocessor, a CPU, central processing unit, field programmable gate array (FPGA), or digital signal processor (DSP)) having stored executable software for determining information indicative of particle size of the particles in the sample 5 by analyzing the detected secondary electromagnetic radiation 6 in accordance with the principle of dynamic light scattering (DLS). The particle size determining unit 22 is configured for determining the information indicative of particle size under consideration of information indicative of the refraction index of the sample 5, as determined by a refraction index determination unit 20 which will be described below in further detail. Thus, in contrast to conventional approaches, there is no need for a user to input a value of the refraction index of the solvent of the sample 5 manually. In contrast to this, the precise value of the refraction index of the sample 5 is determined intrinsically within the apparatus 10 together with the determination of the particle size distribution of the sample 5. This not only significantly more accurate because actually measured values of the refraction index of the sample 5 are usually more precise than literature values, but also allows to analyze the same probe, i.e. the secondary electromagnetic radiation 6, for determining both particle size information and refraction index value. Hence, two directly comparable pieces of information can be determined substantially without significant additional hardware or software expenses.

The refraction index determination unit 20 can for instance comprise a processor (wherein refraction index determination unit 20 and particle size determination unit 22 can be embodied to share one and the same processor, or may have separate processors) having stored executable software for determining information indicative of a value of the refraction index of the sample 5. The refraction index determination unit 20 is configured for determining the information indicative of the refraction index of the sample 5 based on an analysis of the detected secondary electromagnetic radiation 6. Hence, the electromagnetic radiation detector 7 supplies a detection signal to both the refraction index determination unit 20 (as a basis for the determination of the value of the refraction index of the solvent of the sample 5) and the particle size determination unit 22 (as a basis for the determination of the particle size distribution of the particles of the sample 5). Thus, the secondary electromagnetic radiation 6 cannot only be used as a probe carrying information concerning the particle size, but may be synergetically used also for derive information concerning the refraction index of the sample 5. For this purpose, the refraction index determination unit 20 comprises movable optical element 4, which is here embodied as an optically transparent double convex lens. The movable optical element 4 is arranged in an optical path along which the secondary electromagnetic radiation 6 propagates after interacting with the sample 5. The refraction index determination unit 20 is configured for determining information indicative of the refraction index of the sample 5 by analyzing an intensity variation of the detected secondary electromagnetic radiation 6 for different positions of the movable optical element 4 in the optical path. In other words, when the optical element 4 is moved perpendicular or parallel to the propagation direction of the secondary electromagnetic radiation 6, the intensity of the secondary electromagnetic radiation 6 varies. It has been surprisingly found that moving the optical element 4 relative to the optical path of the secondary electromagnetic radiation 6 may balance out or at least partially compensate beam offset (or mismatch) in the event of a change of the value of the refraction index. More specifically, the refraction index determination unit 20 is configured for determining the information indicative of the refraction index of the sample 5 based on a comparison of a maximum intensity (as detected by the electromagnetic radiation detector 7 when the optical element 4 is located at an optimum position in the beam path) with predetermined data of reference solvents (wherein for multiple different reference solvents, the predetermined data may indicate for which position of the optical element 4 the respective maximum intensity can be achieved for a certain solvent having a certain value of the refraction index). The maximum intensity relates to a maximum of the intensity value which can be detected by the electromagnetic radiation detector 7 when the movable optical element 4 is presently located at an optimum position relative to the optical path. The predetermined data of reference materials may refer to a characteristic correlation between a respective position of the optical element 4 relative to the optical path of the secondary electromagnetic radiation 6 and an intensity value detected by the electromagnetic radiation detector 7 when the material of the sample 5 is substituted by the material of the respective reference material (see FIG. 9). When the values of the refraction index is known for the respective reference materials, a comparison of the maximum intensity achievable with a sample 5 (having a certain value of the refraction index) with the maximum intensity values of the reference materials (with the known values of the refraction index) allows to derive the refraction index value of the material of the sample 5 as well. If desired, an extrapolation or interpolation of the data for the reference materials can be made so as to determine the value of the refraction of the sample 5, or more precisely of the solvent thereof.

Although comparison of maximum intensity values of reference materials and the sample 5 allows to determine the value of the refraction index of the sample 5 with particularly high accuracy, it is also possible that other features of a characteristic curve of the intensity distribution obtained for the sample 5 and the reference materials, respectively, are compared so as to determine the value of the refraction index of the sample 5 based on known values of the refraction index for the reference materials in combination with known characteristic curves as reference data.

The apparatus 10 comprises also an adjustment unit 24 configured for moving the optical element 4 to adjust its position so as to at least partially compensate for a deviation between a maximum detection intensity and an actual detection intensity. The adjustment unit 24 may also be embodied as a processor. The adjustment unit 24 on the one hand and at least one of the refraction index determination unit 20 and the particle size determination unit 22 on the other hand can be embodied to share one and the same processor, or to have separate processors. The adjustment unit 24 may control motion of the optical element 4 relative to the beam path (defined by the propagation of the secondary electromagnetic radiation 6 or by the propagation of the primary electromagnetic radiation 2) so that the intensity measured by the electronic radiation detector 7 in terms of a particle size distribution measurement has a sufficiently large value (for instance a value being at least a predetermined threshold value or a value about the predetermined threshold value or even a maximum value). For example in a scenario in which the dynamic light scattering apparatus 10 has drifted away from a default mode with a high detection intensity the adjustment unit 24 may move the movable element 4 until the detected intensity assumes or exceeds the predetermined threshold value.

In a further embodiment, illustrated in FIG. 1*b*, FIG. 2*b* and FIG. 3*b*, the optical element 4 can be located in the laser path rather than in the detection path. It is possible that the laser beam is not orthogonal to the input window of the cuvette or other sample holder, and is therefore dependent on their refraction index. The detection path however is aligned orthogonal to the outlet window and is therefore independently of the refraction index of the sample. However, alternatively, it is possible that the laser beam is orthogonal to the cuvette or sample holder and the detection can be performed via a non-orthogonal angle. In this alternative it would however be possible that the beam displacement now is equilibrated in the detection path. All above described embodiments (lens displacement, mirror displacement, glass plate, wedge, etc.) are also possible in the laser path rather than in the detection path. In other words, when the optical element 4 is moved perpendicular or parallel to the propagation direction of the primary electromagnetic radiation 2, the intensity of the secondary electromagnetic radiation 6 varies. It has been surprisingly found that moving the optical element 4 relative to the optical path of the primary electromagnetic radiation 2 may balance out or at least partially compensate beam offset (or mismatch) in the event of a change of the value of the refraction index. Between the electromagnetic radiation source 1 and an inlet window of the sample container containing the sample 5, a movable optical element 4, here embodied as a lens, is located in the beam path. Depending on its position relative to the beam path, the primary electromagnetic radiation 2 is refracted by the moveable optical element 4 to a certain degree. Between the outlet window of the sample container containing the sample 5 and the radiation detector 7, a fixed optical element 9, here embodied as a lens, is located in the beam path.

The dynamic light scattering (DLS) apparatus 10 shown in FIG. 1a to FIG. 3a and FIG. 1b to FIG. 3b allows to determine the value of the refraction index required for the particle size distribution determination, directly with the DLS apparatus 10. Also, a drift compensation is possible with the DLS apparatus 10. For both determination of the refraction index and drift compensation, the movable optical element 4 may be displaced in a perpendicular or parallel direction with regard to the primary electromagnetic radiation 2 or regarding the secondary electromagnetic radiation 6. On the one hand, drift compensation may be carried out by measuring the intensity of the detection signal by the electromagnetic radiation detector 7 and locating the optical element 4 in such a position relative to the optical beam that a maximum intensity is achieved. Long-term drift due to ageing effects, modified external conditions, etc. may therefore be efficiently compensated without the need of a user intervention. At the same time, a measurement of the characteristic curves of the intensity as a function of the position of the movable optical element 4 relative to the primary electromagnetic radiation 2 or the secondary electromagnetic radiation 6, when compared to predetermined calibration values of known solvents with known refraction indices, may allow for a precise determination of the refraction index of the present sample 5 (in particular a solvent thereof), by simply comparing a measured characteristic curve with data in a look-up table, an interpolation or extrapolation with the calibration values, etc.

A significant advantage of the DLS apparatus 10 as compared to alternative measurement techniques is that only a very small amount of pre-knowledge is sufficient with regard to the properties of the sample 5. Conventionally, a user has to input the value of the refraction index and the viscosity of the solvent of the sample 5 into a DLS apparatus. Both properties only relate to the solvent, not the actual particles dispersed in the solvent. It is hence not necessary that the material of the particles is known. It is sufficient that the material of the dispersion medium, i.e. of the solvent, is known. Additionally, temperature, wavelength of used electromagnetic radiation 2, 6 and a scattering angle influence the calculation of the particle size distribution. However, some of these parameters are device parameters and need not be input by a user. Temperature may be provided by a user or may be measured, and can be regulated by the DLS apparatus 10 and controlled by a temperature measurement.

The refraction index of the solvent of the sample 5 is required for the analysis of the particle size information, because the wavelength of the measurement laser (or other type of electromagnetic radiation source 1) depends on the medium of the dispersion. The nominal laser wavelength usually refers to vacuum and is therefore not relevant for the scattering procedure within the sample. In the medium, the speed of light and therefore the wavelength are reduced (the frequency remains the same). The factor of this reduction is the refraction index. The refraction index has an impact on the calculation of the scattering vector and consequently on the calculation of the diffusion coefficient and the particle size.

For a diluted sample 5, the refraction index of the sample 5 can be set equal to the refraction index of the solvent. In these cases, the refraction index can be determined directly in the dispersion to be measured, and no additional sample with pure solvent is required.

Conventional DLS apparatuses provide a possibility to input the parameter of the sample properties. In particular, the type of solvent has to be input in a conventional approach. However, there are certain applications in which the refraction index is not known beforehand. This is for instance the case when mixtures of different solvents are present or the concentration of dissolved substances (for instance salts) is unknown. In these cases, in order to avoid measurement errors, the precise refraction index has to be measured separately in conventional DLS apparatuses.

According to an exemplary embodiment of the invention, the measurement of the refraction index can be performed with the DLS detector (i.e. the electromagnetic radiation detector 7), in particular at a scattering angle of 90°. At this angle, the measurement geometry is dependent on the refraction index. However, it is also possible to measure the refraction index at other measurement angles in side-scattering direction. The expression "side scattering direction" is meant to include scattering angles of the detected light beam having directional components perpendicular to the direction of the irradiation of laser beam.

In an embodiment, the primary electromagnetic radiation 2 (also denoted as incident laser beam) does not impinge horizontally into a rectangular measurement cell or sample container, but may propagate with about 0.5-10° from an upper region to a lower region. This can be achieved by arranging a collective lens as movable optical element 4 not centrally aligned with the focused laser beam, but slightly above the center. Upon entry into the measurement cell, the laser beam is refracted. That means that the effective angle with which the laser beam propagates downwardly within the measurement cell depends on the refraction index of the sample 5. If the refraction index was 1 (i.e. air or vacuum), the laser beam would propagate downwardly through the cell with 0.5-10° without being refracted. The higher the value of the refraction index is, the flatter the beam propagates in the sample 5. A preferred impinge angle of the electromagnetic radiation 2 will be about 3°. The wall of the cell is not taken into account in this consideration, but only results in a parallel displacement of the beam defined by electromagnetic radiation 2, 6, respectively and does not result in the change of the direction of the respective beam of electromagnetic radiation 2, 6.

FIG. 4 shows the laser beam directly upstream (primary electromagnetic radiation 2) and within the sample 5, more precisely a sample container containing a dispersion of a solvent with particles under analysis. The primary electromagnetic radiation beam 2 passes the movable optical element 4 embodied as collective lens, and subsequently the measurement cell. The collective lens focuses the laser beam in a centrum of the measurement cell and creates a non-orthogonal incident angle on the inlet window of the cell. When entering and leaving the cell, the laser beam is refracted.

The DLS detector, i.e. the electromagnetic radiation detector 7, is arranged at a scattering angle of 90° so that there is no refraction index dependence for the scattered light. The scattered light is detected in an orthogonal direction with regard to the cell wall. Hence, there is no change of the detection angle with a change of the refraction index of the sample 5, and the electromagnetic radiation detector 7 is consequently oriented independently of the refraction index value always along one and the same predefined direction.

The described geometry results in the situation, that the DLS apparatus 10 is aligned for a certain refraction index of the sample 5. If a sample 5 with another value of the refraction index is used, there is a certain deviation of the beam path. The laser beam changes its direction, whereas the detection beam remains unchanged. The intersection point of both is lost and the detected scattering intensity is reduced. This effect is absolutely desired in terms of exemplary embodiments of the invention and has the consequence that only a sample 5 with a certain value of the refraction index is measured efficiently at a scattering angle of 90°.

FIG. 5 shows a side view of the measurement cell or sample container accommodating the sample 5. Reference numeral 50 denotes a beam path for water (value of the refraction index n=1.33) as solvent of the sample 5, reference numeral 52 denotes a beam path for toluene (n=1.50) as solvent of sample 5, and reference numeral 54 denotes a viewing direction of the electromagnetic radiation detector 7 (not shown). A horizontal position is plotted along an abscissa 60, whereas a vertical position is plotted along an ordinate 62. The viewing direction (perpendicular to the paper plane of FIG. 5) is along the detection direction. The different beam paths 50, 52 in FIG. 5 relate to the path of the laser beam for different media. Depending on the refraction index, the laser is refracted to different amounts. The DLS detector or electromagnetic radiation detector 7 can have a spatial filter upstream thereof. That means, the electromagnetic radiation detector 7 accepts or detects only light coming from a certain direction. This can be realized with a fiber optic (not shown). The detection path is oriented orthogonal to the outlet window of the scattered beam and orthogonal to the paper plane of FIG. 5. For a medium with a given value of the refraction index (for instance water, see reference numeral 50), the DLS apparatus 10 has an optimum orientation or alignment. That means that laser beam and detector beam intersect in an optimum manner and form in an overlapping range the so-called scattering volume. Only particles within this volume are illuminated by the laser beam, as well as are detected by the electromagnetic radiation detector 7. When the medium is substituted by another medium with another refraction index (for instance toluene, see reference numeral 52), the refraction angle is modified. Thus, the optimum intersection is lost and the overlapping volume is reduced or vanishes completely. This results in a reduction of the detected scattering intensity.

According to an exemplary embodiment of the invention, the movable optical element 4 (here embodied as a collective lens) is movably mounted. By a step motor (not shown), the lens can be moved out of a central position by a predefinable amplitude of for instance 5 mm in or against the laser light propagation direction. With this degree of freedom it is possible, to at least partially compensate for the above described beam deviation and to measure at the maximum of the scattering intensity for each desired refraction index value. For this purpose, an algorithm may be integrated in a software of the scattering apparatus 10 which optimizes, prior to each measurement, the position of the movable optical element 4. The criterion for this automatic adjustment may be to achieve the maximum of the detected intensity or to obtain a detected intensity above a predefined threshold value.

Figure 6:
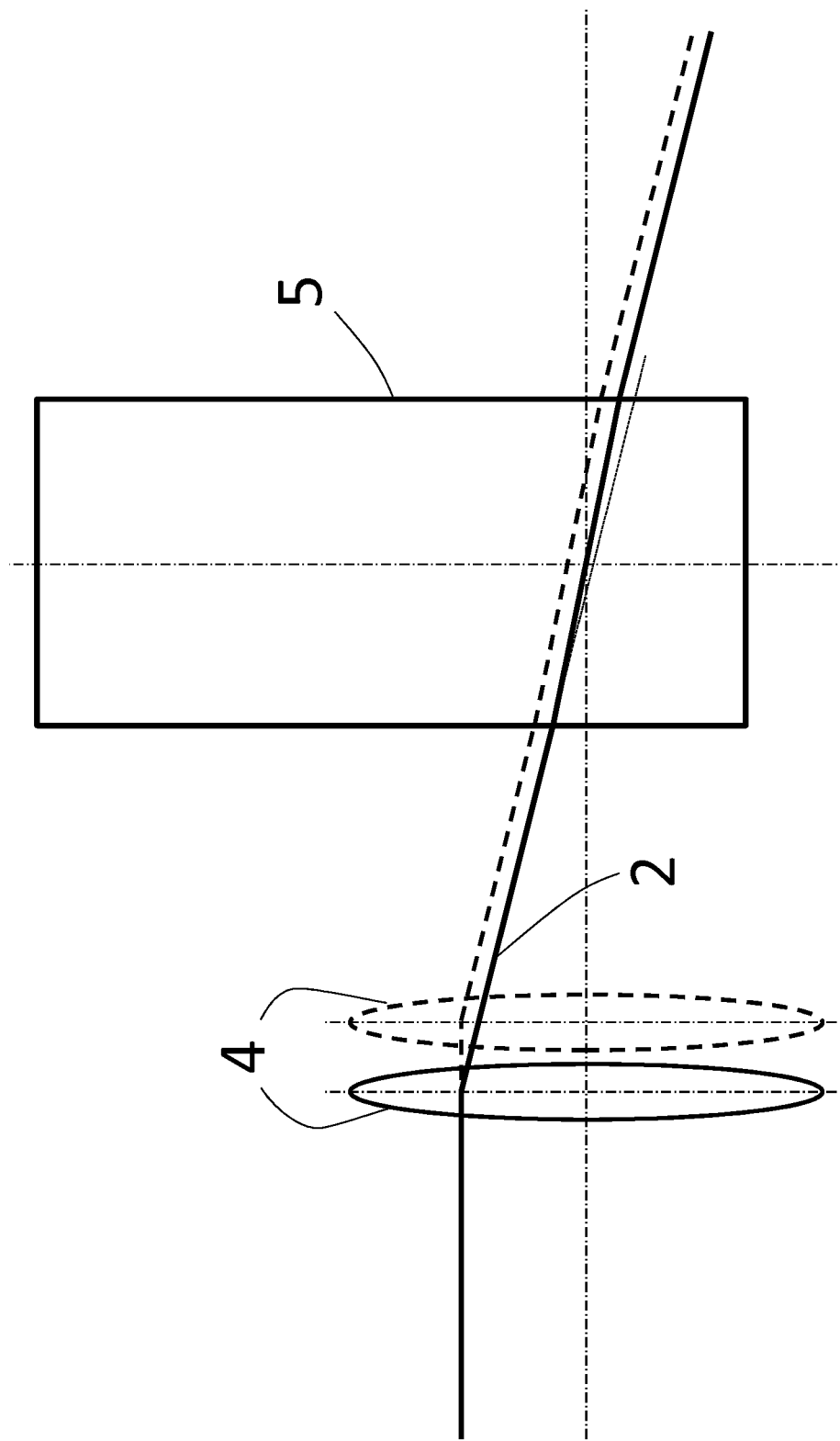
FIG. 6 is a schematic view of a displacement of a collective lens as an optical element according to an exemplary embodiment of the invention.

FIG. 6 is a schematic illustration showing the displacement of the movable optical element 4, here embodied as collective lens. By a displacement of the collective lens along the laser axis, the laser beam can be displaced parallel within the sample 5.

Figure 7:
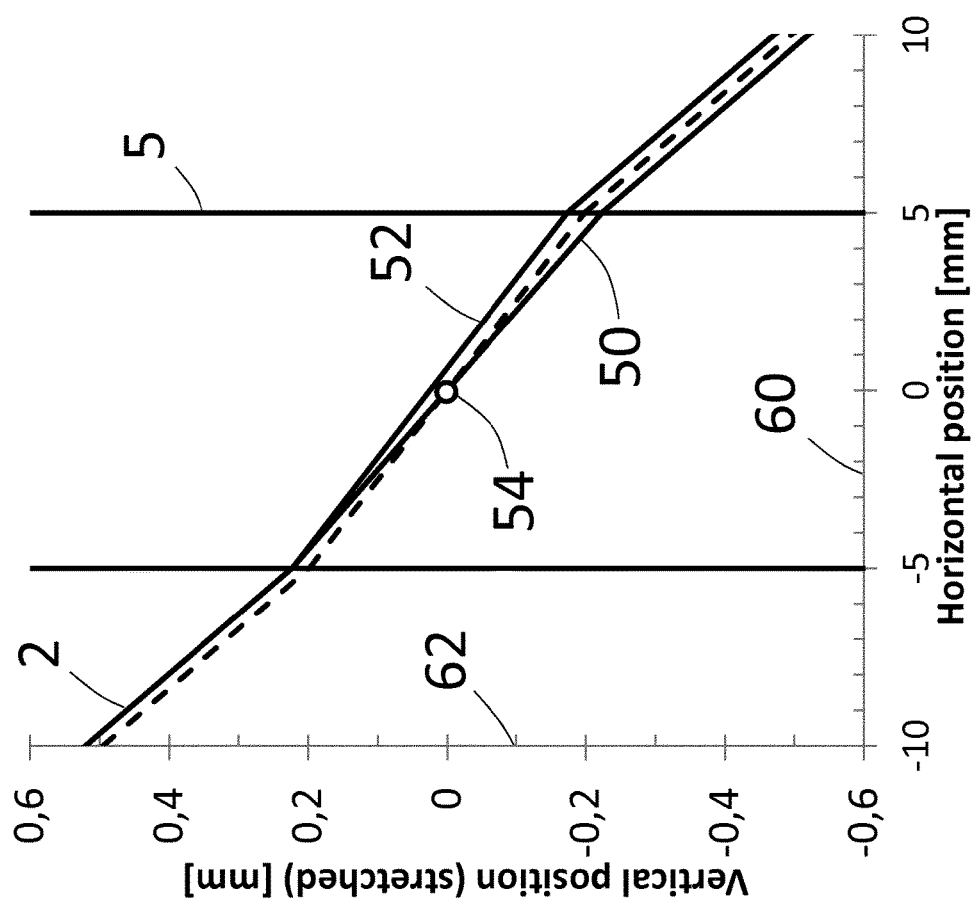
FIG. 7 shows optimum measurement positions for samples with different refraction index values.

FIG. 7 shows an optimum measurement position for samples 5 with different values of the refraction index. In order to compensate for a beam displacement when changing from water to toluene (or more generally from a sample 5 having a solvent with a lower value of the refraction index to another sample 5 having a higher value of the refraction index), the collective lens has to be displaced slightly with regard to the beam direction, in order to maintain an optimum intersection with the detector beam.

It has been found in terms of the present invention that the aforementioned phenomenon advantageously provides also the possibility of determining the refraction index of the sample 5. The optimum position of the collective lens is dependent on the value of the refraction index of the sample 5. When the DLS apparatus 10 is calibrated by the measurement of two samples 5 with known value of the refraction index and has been adjusted correspondingly, the refraction index of unknown samples 5 can be determined based on the optimum lens position during the motion.

In the following, it will be explained how the experimental adjustment of the optimum measurement position and an automatic fine-tuning or fine-adjustment of the DLS apparatus 10 may be carried out according to an exemplary embodiment of the invention. As mentioned above, the DLS apparatus 10 has a provision for displacement of the collective lens for correcting the refraction index. This adjustment may be carried out automatically by a software using a step motor (for instance having an adjustment range of +/−5 mm).

Figure 8:
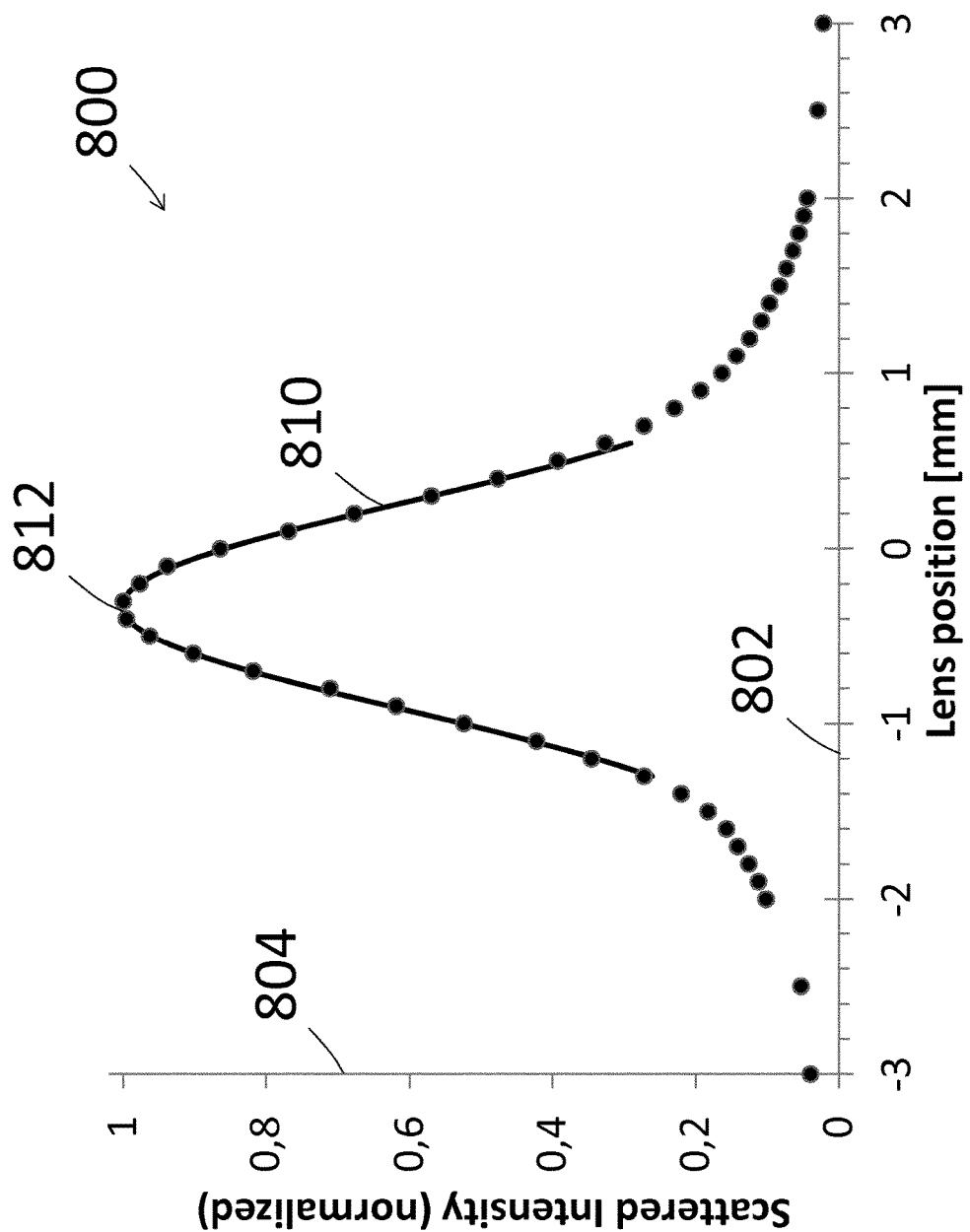
FIG. 8 is a diagram illustrating an experimentally obtained curve for determining an optimum measurement position by a displacement of a movable optical element in the form of a collective lens along a laser beam path according to an exemplary embodiment of the invention.

FIG. 8 shows a diagram 800 having an abscissa 802 along which the lens position is plotted in mm. Along an ordinate 804, the scattered intensity is plotted, as detected by the electromagnetic radiation detector 7. Hence, FIG. 8 shows the dependency of the detected scattering intensity as a function of the lens position for a certain solvent of the sample 5.

As can be taken from FIG. 8, a relatively broad symmetric characteristic curve 810 having a maximum 812 of the intensity value with a full width half maximum (FWHM) of slightly above 1 mm is obtained. In order to measure at a practically maximum scattering intensity, it is advantageous if the position can be adjusted with an accuracy of at least 0.1 mm. An automatic search algorithm implemented in the software of the DLS apparatus 10 can perform this task. It may be executed prior to each DLS measurement and may allow to adjust the optimum measurement point for each sample 5. The DLS apparatus 10 may hence carry out an automatic fine adjustment of the optics prior to each measurement. Apart from the compensation of refraction index differences, it is also possible to obtain an improvement of the long-term stability. Drifts (for instance due to mechanical changes of the position of components of the DLS apparatus 10 and/or changes in the emission characteristic of the light source) over a long term may be balanced or compensated for, so that the accuracy of the measurement can be maintained continuously high over a long term with an optimum overlap of laser and detector beam.

Hence, FIG. 8 shows the experimental determination of the optimum measurement point by a displacement of the collective lens along the laser beam. This optimum measurement point corresponds to the maximum 812 of the detected scattering intensity, in the shown example at −0.32 mm. An aqueous suspension with latex particles with a 100 nm particle size has been used for FIG. 8. The solid line shows a least square fit with a Gaussian curve. This fit allows for a precise determination of the position of the maximum 812 of the intensity.

Figure 9:
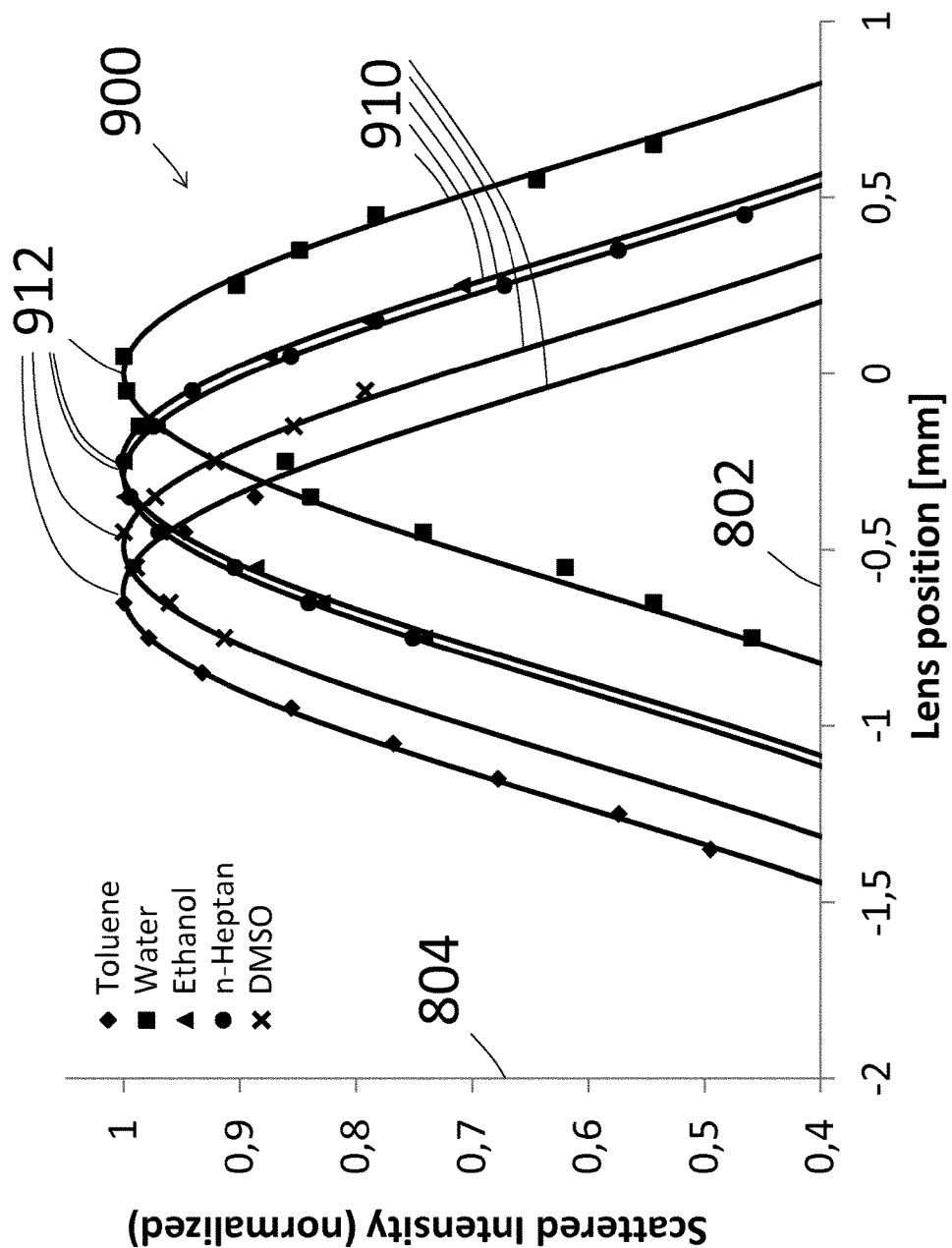
FIG. 9 shows different characteristic curves indicative of the detection intensity as a function of a position of a movable optical element for different solvents as used according to an exemplary embodiment of the invention.

Next, the determination of optimum measurement positions for different solvents will be described. The determination of the optimum measurement point for different solvents can be repeated for different solvents. Pure solvents can be used. This means that no particles need to be added and the detected scattering intensity can be correspondingly small. Using pure solvent requires the use of the absence of dust particles or the like. The presence of such artificial particles may result in spikes of the scattering signal and may result in problems for determining the maximum. FIG. 9 shows the result of the experiments.

FIG. 9 shows a diagram 900 again having abscissa 802 and ordinate 804. The intensity of the respective detection signal is plotted for different pure solvents see the various characteristic curves 910. The experimental data have also been fitted with a Gaussian function. The width of the Gaussian function remains unchanged, and the position of the maximum 912 is the only fitting parameter.

As can be taken from FIG. 9, the optimum measurement point (i.e. maximum 912 of the detection intensity) for the various solvents can be found at different positions of the collective lens as movable optical element 4. This results from the different values of the refraction index. Water has the smallest refraction index among the shown solvents and causes the smallest refraction of the laser beam. Toluene has the highest refraction index value among the shown solvents and causes the largest refraction. The optimum positions scale with the value of the refraction index of the respective solvent.

In the following, the determination of the refraction index from the position of the intensity maximum will be described.

When calculating and adjusting the position of the collective lens at the intensity maximum value with two solvents having known refraction indices (for instance water and toluene), this allows to determine the value of the refraction index for unknown solvents.

Table 1 shows experimental values for the determination of the refraction index. Water and toluene have been used for the adjustment. This adjustment yielded the calculated values of the refraction indices (n) of the other solvents. The determined adjustment function is:

$RI = 0.7891 - 0.2775 \times (\text{position of the maximum})$

TABLE 1

| Solvent | n (literature value) | Position maximum [mm] | n (calculated) | Absolute error | Relative error [%] |
|---|---|---|---|---|---|
| Water | 1.3302 | −1.95 | — | — | — |
| Ethanol | 1.3636 | −2.10 | 1.372 | 0.008 | 0.6 |
| n-Heptane | 1.387 | −2.15 | 1.386 | −0.001 | −0.1 |
| DMSO | 1.479 | −2.45 | 1.469 | −0.010 | −0.7 |
| Toluene | 1.4967 | −2.55 | — | — | — |

Hence, it has been possible to determine the refraction index with a relative error of less than 1%.

In the following, the geometrical beam path will be analyzed.

The refraction of the light beam at the border surface can be calculated with Snell's refraction law. For a given geometry and refraction index, the beam path can be calculated. The beam paths in water and toluene with the DLS apparatus 10 are shown in FIG. 7. For the compensation of the difference of the refraction index, a lens displacement of 0.63 mm is appropriate.

Hence, experimentally, a position displacement of the maximum between water and toluene of 0.60 mm has been found (see Table 1). Therefore, experiment and theory are in good agreement.

In the following, the influence of an error of the refraction index on the result of the DLS measurement will be described.

An analysis of the individual steps of the DLS algorithm allows an evaluation of the error propagation of the refraction index up to the end result, i.e. the particle size.

The refraction index n has an impact on the calculation of the scattering vector q:

$$q = \left(\frac{4\pi n}{\lambda_0}\right)\sin\left(\frac{\theta}{2}\right)$$

In the above formula, $\lambda_0$ is the wavelength of the laser in the vacuum and e is the scattering angle. In a further consequence, the scattering vector q is required in order to fit the experimental correlation function $G(\tau)$:

$G(\tau) = A[1 + B \exp(-2\Gamma\tau)]$

In the before mentioned formula, $\tau$ is the correlation time, A and B are device constants. The scattering vector q has an impact on the relaxation constant $\Gamma$ which is defined as follows:

$\Gamma = Dq^2$

From the fit, the diffusion constant D can be determined and the hydrodynamic radius $R_o$ can be calculated, using the Stokes-Einstein relation:

$$R_0 = \frac{k_B T}{6\pi\eta D}$$

In the before mentioned formula, the Boltzmann constant $k_B$, the absolute temperature T and the viscosity of the solvent $\eta$ have an influence.

The described considerations can be implemented in the DLS apparatus shown in FIG. 1a to FIG. 3a and FIG. 1b to FIG. 3b.

Hence, differences in the beam path of different refraction indices may be compensated by a displacement of the collective lens. One advantageous aspect is to obtain an optimum measurement geometry for DLS at a scattering angle of 90° independent of the refraction index of the sample 5. The accuracy of the determination of the maximum of 0.1 mm is sufficient, in order to carry out the measurement always with an optimum intensity. Furthermore, the long-term drift is equilibrated and the long-term stability of the DLS apparatus 10 is increased. The DLS apparatus 10 can be fine-tuned prior to each measurement. A further advantage is the possibility to determine the refraction index of the sample 5. The DLS apparatus 10 can be calibrated and adjusted with two samples 5 with known values of the refraction index. In this context, it is possible to use pure solvents (it is possible but not necessary to use a dispersion).

When the determination of the refraction index requires an even higher accuracy of for example 0.01 mm, this can be obtained by a sufficiently long integration time, a sufficiently small step width and a refined determination of the maximum.

Thus, a user has the opportunity to determine the refraction index for samples 5 with unknown solvent directly within the DLS apparatus 10 and to use this as an input parameter for the particle size determination.

Figure 10:
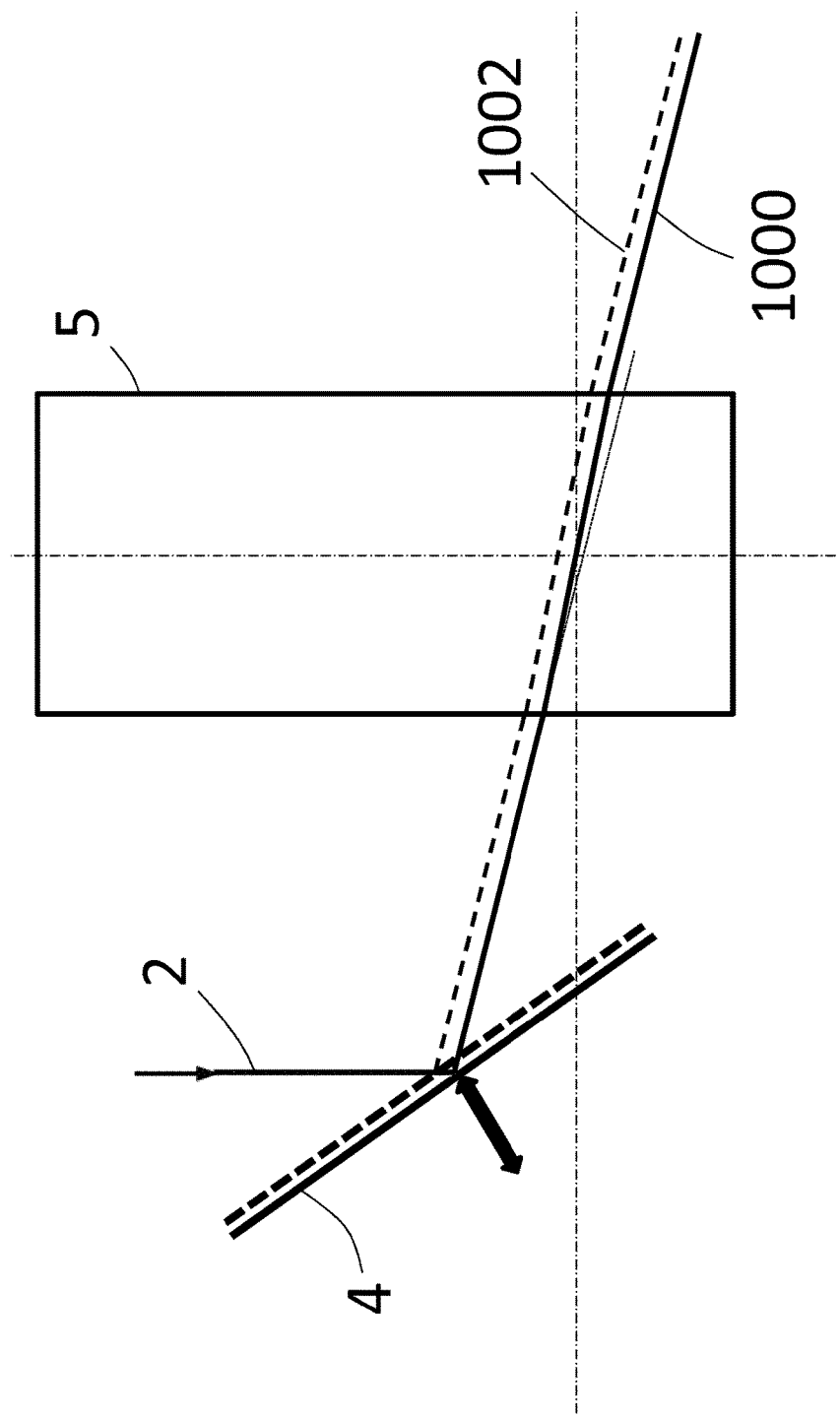
FIG. 10 shows a movable optical element embodied as a mirror according to an exemplary embodiment of the invention.

As can be taken from FIG. 10, the movable optical element 4 can also be realized by a mirror (or more generally a reflective optical element 4) rather than by a lens (or more generally a transmissive optical element 4). Also this allows a parallel displacement of the incident laser beam. Line 1000 shows the beam path with the mirror at a first position, line 1002 shows the beam path with the mirror at a second position.

Figure 11:
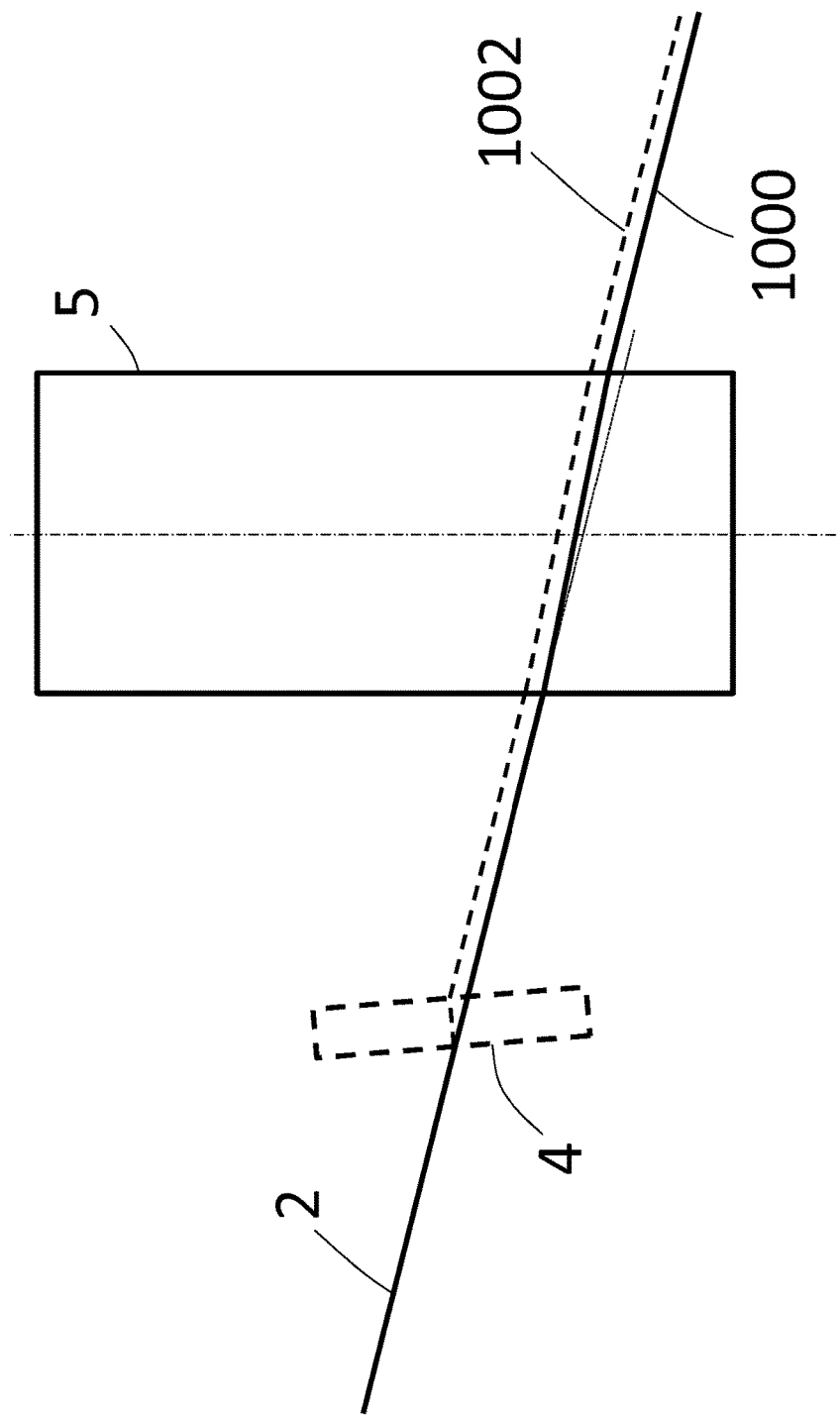
FIG. 11 shows a movable optical element embodied as a displaceable glass plate according to an exemplary embodiment of the invention.

As can be taken from FIG. 11, a further alternative is the use of a plan parallel glass plate as movable optical element 4. More specifically, FIG. 11 shows an embodiment of the invention with a substitutable glass plate which is inserted (for instance in an oblique or inclined way) into the beam path. Line 1000 shows the beam path without glass plate, line 1002 shows the beam displacement after the insertion of the glass plate as movable optical element 4. For different refraction indices, glass plates of different thickness can be provided and can be moved in or moved out of the beam path. Depending on the thickness of the glass plate, the laser beam is displaced to a certain amount. The substitution of glass plates can be performed automatically, for instance by an optic revolver which comprises multiple glass plates with different thicknesses. Turning the revolver turns or moves the glass plates relative to the beam path.

Figure 12:
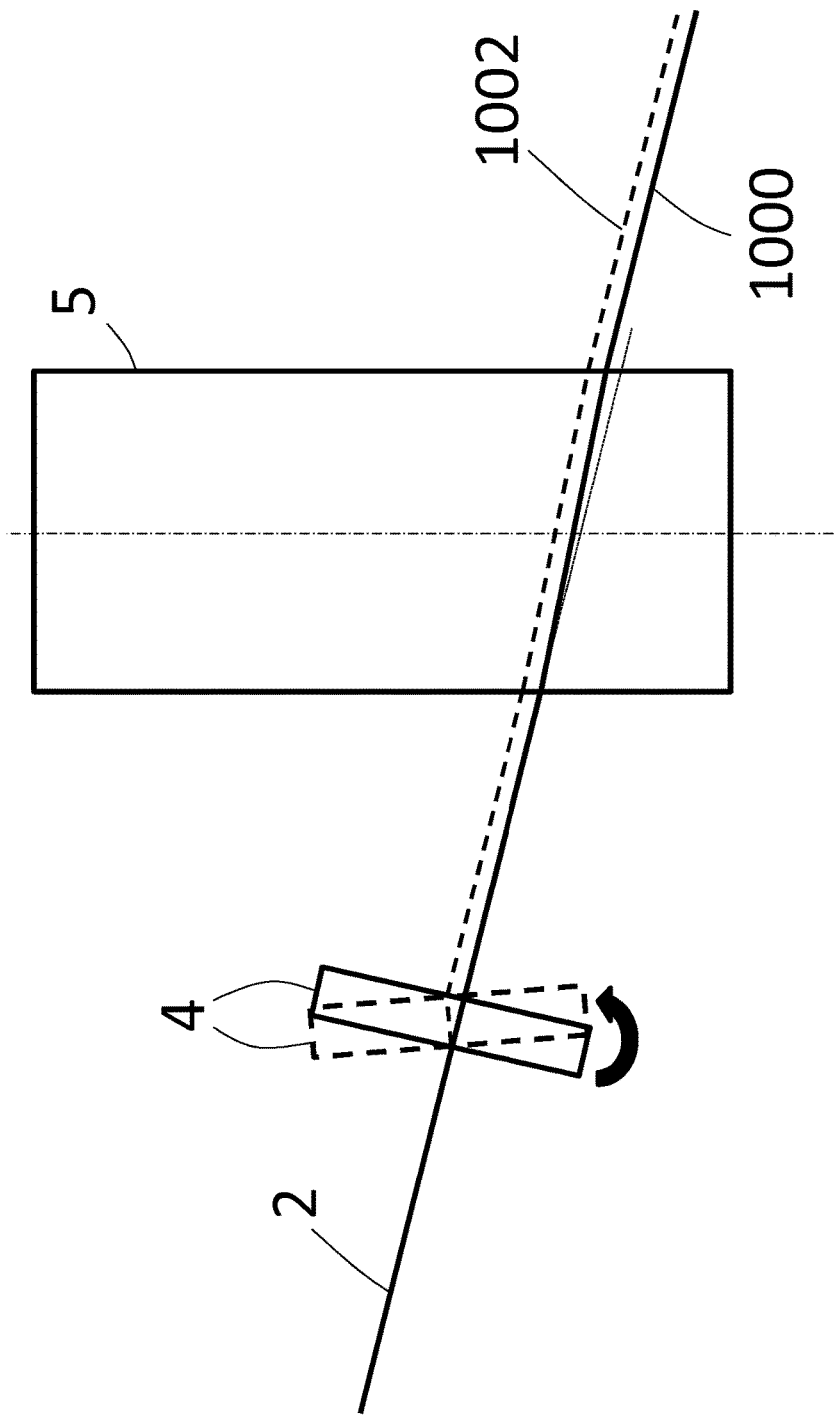
FIG. 12 shows a movable optical element embodied as a tiltable glass plate according to an exemplary embodiment of the invention.

FIG. 12 shows a further embodiment of the movable optical element which is here realized by a tiltable glass plate. Depending on the incident beam direction and corresponding angle with regard to the glass plate, the laser beam can be displaced to different extents, see lines 1000 and 1002.

Figure 13:
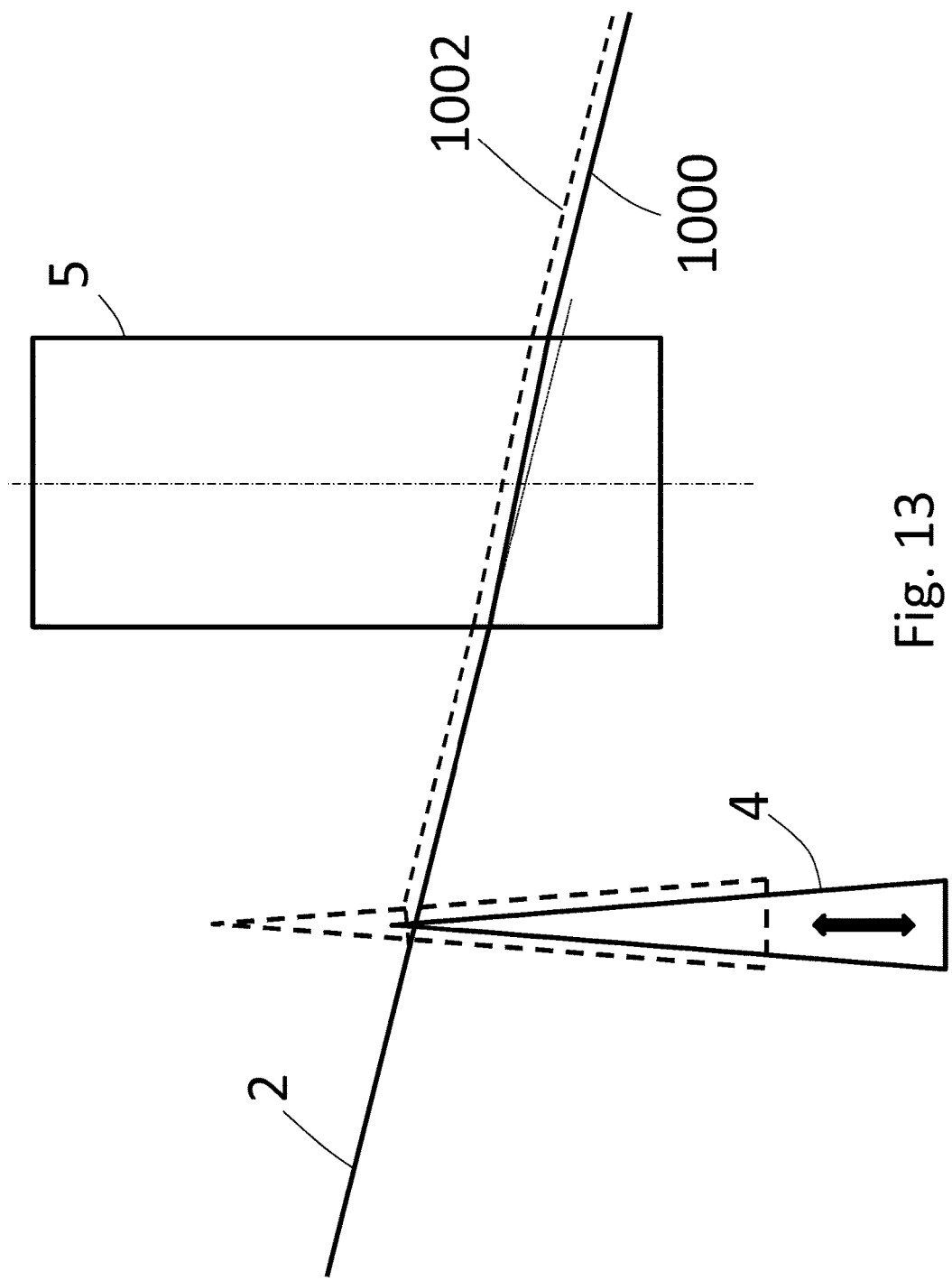
FIG. 13 shows a movable optical element embodied as a displaceable wedge according to an exemplary embodiment of the invention.

FIG. 13 shows a further embodiment of the movable optical element 4, which is here realized by a displaceable wedge. The wedge can be inserted to a variable extent into the laser beam. Depending on the path length of the glass body, the displacement of the laser beam can be adjusted, see lines 1000 and 1002. Additionally, there is a directional displacement which is however independently of the position of the wedge.

All above described embodiments (lens displacement, mirror displacement, glass plate, wedge, etc.) are also possible in the detection path rather than in the illumination path.

A further alternative is to use a non-orthogonal impinging angle on the cuvette wall both upstream and downstream of the sample holder. In principle, it is possible that both light paths are non-orthogonal with regard to the cuvette wall. As long as the impinging angles are different from one another, a change of the refraction index also results in a reduction of the detected intensity due to a misalignment. The parallel alignment by one of the above-mentioned optical elements 4 can be performed in the laser path and/or in the detected beam path.

It should be noted that the term "comprising" does not exclude other elements or steps and the "a" or "an" does not exclude a plurality. Also elements described in association with different embodiments may be combined.

It should also be noted that reference signs in the claims shall not be construed as limiting the scope of the claims.

Implementation of the invention is not limited to the preferred embodiments shown in the figures and described above. Instead, a multiplicity of variants are possible which use the solutions shown and the principle according to the invention even in the case of fundamentally different embodiments.

The invention claimed is:

1. A scattering apparatus, in particular a dynamic light scattering apparatus, comprising:
   an electromagnetic radiation source configured for irradiating a sample with primary electromagnetic radiation;
   an electromagnetic radiation detector configured for detecting secondary electromagnetic radiation generated by scattering the primary electromagnetic radiation at the sample;
   a refraction index determination unit configured for determining information indicative of a refraction index of the sample; and
   a particle size determining unit configured for determining information indicative of particle size of particles in the sample by analyzing the detected secondary electromagnetic radiation;
   wherein the refraction index determination unit comprises a movable optical element in an optical path along which at least one of the primary electromagnetic radiation and the secondary electromagnetic radiation propagates and is configured for determining information indicative of the refraction index of the sample by analyzing an intensity variation of the detected secondary electromagnetic radiation at different positions of the movable optical element in the optical path.

2. The apparatus according to claim 1, wherein the refraction index determination unit is configured for determining the information based on a correlation between an intensity of the detected secondary electromagnetic radiation and a variable position of the optical element relative to an optical path along which at least one of the primary electromagnetic radiation and the secondary electromagnetic radiation propagates, which correlation is dependent on a value of the refraction index of the sample.

3. The apparatus according to claim 1, wherein the refraction index determination unit is configured for determining the information indicative of the refraction index of the sample based on a comparison of:
   a feature of an intensity curve obtained during the intensity variation; and
   predetermined data of reference materials indicative of a correlation between refraction index value and a detected feature of a reference intensity curve of the reference materials.

4. The apparatus according to claim 1, wherein the optical element is selected from a group consisting of a lens, a mirror, a plate, and a wedge.

5. The apparatus according to claim 1, wherein the optical element is located:
   between the electromagnetic radiation source and the sample; or
   between the sample and the electromagnetic radiation detector.

6. The apparatus according to claim 1, wherein the optical element is mounted so as to be movable by at least one of the group consisting of displacing the optical element along or parallel to the optical path, displacing the optical element perpendicular to the optical path, and tilting the optical element relative to the optical path.

7. The apparatus according to claim 1, comprising an adjustment unit configured for moving the optical element so as to at least partially compensate for a deviation between a maximum detection intensity and an actual detection intensity.

8. The apparatus according to claim 1, wherein the particle size determining unit is configured for determining the information indicative of particle size under consideration of the determined information indicative of the refraction index.

9. The apparatus according to claim 1, wherein the electromagnetic radiation detector is located, for detecting secondary electromagnetic radiation for determining the information indicative of the refraction index, to detect the secondary electromagnetic radiation along a secondary propagation direction which is oriented to detect beam components oriented perpendicular to the primary electromagnetic radiation.

10. A method of determining information indicative of particle size of particles in a sample by scattering, in particular by dynamic light scattering, wherein the method comprises:

irradiating a sample with primary electromagnetic radiation from an electromagnetic radiation source;

detecting, by an electromagnetic radiation detector, secondary electromagnetic radiation generated by scattering the primary electromagnetic radiation at the sample;

determining information indicative of a refraction index of the sample by a refraction index determination unit; and determining information indicative of particle size of particles in the sample by analyzing the detected secondary electromagnetic radiation by a particle size determination unit;

wherein the refraction index determination unit comprises a movable optical element in an optical path along which at least one of the primary electromagnetic radiation and the secondary electromagnetic radiation propagates and is configured for determining information indicative of the refraction index of the sample by analyzing an intensity variation of the detected secondary electromagnetic radiation at different positions of the movable optical element in the optical path.

* * * * *